United States Patent [19]

Barnard

[11] Patent Number: 5,194,645
[45] Date of Patent: Mar. 16, 1993

[54] TRANS-PT (IV) COMPOUNDS

[75] Inventor: Christopher F. J. Barnard, Reading, United Kingdom

[73] Assignee: Johnson Matthey Public Limited Company, London, England

[21] Appl. No.: 848,681

[22] Filed: Mar. 9, 1992

[30] Foreign Application Priority Data

Mar. 9, 1991 [GB] United Kingdom ............. 9105037

[51] Int. Cl.$^5$ .............................................. C07F 15/00
[52] U.S. Cl. .................................... 556/137; 514/492
[58] Field of Search ......................... 556/137; 514/492

[56] References Cited

U.S. PATENT DOCUMENTS 4,329,299 5/1982 Hydes ................................. 556/137
4,394,319 7/1983 Hydes et al. ....................... 556/137

FOREIGN PATENT DOCUMENTS 0328274 8/1989 European Pat. Off. .
0333351 9/1989 European Pat. Off. .
0423707 4/1991 European Pat. Off. .

Primary Examiner—Arthur C. Prescott
Attorney, Agent, or Firm—Cushman, Darby & Cushman

[57] ABSTRACT

Trans-Pt(IV) compounds of general formula $$[PtX_2Y_2L^1L^2)]$$

where X is halogen, Y is halogen, hydroxyl or carboxylate and each L is an amine ligand, providing $L^1$ and $L^2$ are not both $NH_3$ are surprisingly active against cancer cells, in contrast to expectations that all trans-Pt compounds are inactive.

14 Claims, No Drawings

TRANS-PT (IV) COMPOUNDS

This invention concerns improvements in chemical compounds, more especially, it concerns novel platinum-containing compounds with activity against cancer cells.

Since the discovery of antitumour activity for cis-[PtCl$_2$(NH$_3$)$_2$] ("cisplatin") and its widespread adoption as an efficacious drug for the treatment of cancers in patients, there has been a considerable effort by various groups around the world to synthesise new platinum compounds with improved properties. In addition to attempts to find new compounds with activity against different types of cancers and/or with reduced side-effects on patients, there have been attempts to find compounds with activity against cancer cell-lines which exhibit resistance to the commercially-available anti-cancer drugs. If chemotherapy using a platinum-containing compound does not completely eradicate all the cancer cells in a tumour, it is possible for those cells having resistance to the platinum-containing compound to repopulate the tumour. It will then usually be necessary to try other treatments such as other chemotherapeutic agents or radiation therapy.

Cisplatin and the second-generation platinum compound carboplatin [Pt(CBDCA)(NH$_3$)$_2$] where CBDCA=1,1-cyclobutanedicarboxylate which is now being introduced, are cis-Pt(II) compounds. Trans-Pt(II) compounds are widely believed to have little or no selective activity against cancer cells. There is a large body of expert opinion that extensive studies of structure-activity relationships show that only cis-compounds could be expected to show selective anti-tumour activity. For example, one of the earliest structure-activity studies was reported by Cleare in Co-ordination Chemistry Reviews, 12, 349, 1974 which showed that trans-isomers of active cis-Pt compounds such as Cisplatin were inactive. The same author, writing in 1983 in "Structure-Activity Relationships of Anti-tumour Agents", Ed D N Reinhardt et al, Martinus Nijhoff Publishers, The Hague (1983) made it clear that many studies had shown that the trans-isomers were inactive, both for Pt(II) and Pt(IV) compounds. A large number of cis-Pt(IV) compounds have been proposed and some are being studied as potential therapeutic agents. A current theory of the mode of operation of Pt(IV) compounds is that in the body, they are converted to the corresponding Pt(II) compound, and as has already been mentioned, trans-Pt(II) compounds appear to lack desirable activity.

There have been very many patent publications in the art of anti-cancer Pt compounds. These were addressed to the skilled man, and for that reason often did not specify that the compounds were in fact in the cis-isomeric form. As has been said above, the skilled man would have no expectation that any significant activity was being asserted or could be expected for trans-isomers. Additionally, the skilled man would appreciate that the synthetic routes described invariably yield the cis-isomer.

We have now surprisingly discovered that a certain class of trans-Pt(IV) compounds possess useful activity in tests on cancer cells, and exhibit interesting activity against cisplatin-resistant cell lines. Although we do not wish to be bound by any theory, it seems probable that these trans-Pt(IV) compounds act in a different way to that postulated for cis-Pt(IV) compounds.

The present invention provides novel trans-Pt(IV) compounds of general formula I, $$PtX_2Y_2L^1L^2 \qquad I$$

in which each of L$^1$ and L$^2$ is an amine ligand, provided that L$^1$ and L$^2$ are not both NH$_3$, and
each of X and Y is a halogen (especially chlorine), hydroxyl or a carboxylate, or both Y's together form a dicarboxylate or both X's and both Y's together form dicarboxylates, in which the ligands L$^1$ and L$^2$ are in mutually trans co-ordination sites on the platinum atom.

Preferably, X is chlorine and Y is hydroxyl.

Preferred ligands include the primary amines R-NH$_2$, in which R is aralkyl, e.g. benzylamine, or R is straight chain alkyl, eg, of 1 to 10 carbon atoms, more preferably of 1 to 8 carbon atoms, branched chain alkyl, e.g., of 1 to 8 carbon atoms, or cycloalkyl, e.g. of 5 to 7 carbon atoms, and bridged cycloalkyl, e.g. 2-norbornyl, adamantyl. Especially preferred R groups are cycloalkyl, or branched chain alkyl of 3 to 7 carbon atoms. Secondary amines are also suitable, e.g. diethylamine, and tertiary amines, e.g. quinuclidine may also be used. The ligands may also include heterocyclic amines such as morpholine or pyridine.

The compounds of the invention are prepared by a process comprising reacting a trans-Pt(II) compound of formula II, $$\text{trans-}[PtX_2L^1L^2] \qquad II$$

in which L$^1$ and L$^2$ are as defined above, and X is a halogen atom, with a source of the desired group Y, and, where X is OH, replacing the halogen with hydroxyl, and, where Y and/or X is carboxylate or X$_2$ and/or Y$_2$ are dicarboxylate, acylating the corresponding compound of formula I in which Y$_2$ or X$_2$ and Y$_2$ (OH)$_2$ using a monofunctional or difunctional acylating agent.

It will be realised that the process of the invention may take place in one or more steps. In particular, the compound of formula II may be reacted with a source of chlorine, or with hydrogen peroxide, to form a compound of formula Ia or Ib $$\text{trans-}[PtCl_4L^1L^2] \qquad Ia$$

$$\text{trans-}[PtCl_2(OH)_2L^1L^2] \qquad Ib$$

respectively, or in the case where Y is carboxylate, comprising acylation of the corresponding compound Ib, for example using an acid chloride or anhydride.

It is preferred, for convenience and safety, to form the tetrachloro compound Ia by treatment of the corresponding compound Ib with hydrochloric acid as the source of chloride, although oxidation of a compound II with chlorine gas may be used.

The process is suitably carried out in an aqueous medium, with the platinum compounds in solution or in suspension, desirably with heating to about 70° C., and desirably for 1 to 3 hours.

The reaction mixture is then concentrated, chilled and the product is filtered off. Conventional purification steps and confirmatory analysis may then be used.

The above processes and process variants described herein, are within the competence of the experienced platinum chemist, who will be able to choose particular reaction conditions, including particularly solvents, and forms of reactants to optimise yields. In particular, the experienced platinum chemist will be aware that there are differences in hydrophilicity and solubility of the various reactants and final products, and will choose appropriate solvent systems, reaction times and temperatures.

The trans-Pt(II) starting material may be formed by treating a cis-Pt(II) starting material of formula III,

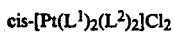     III with hydrohalic acid, especially hydrochloric acid, with heating, which yields the compound of formula II, and the acid salts of the amines $L^1$ and $L^2$.

In turn, the compound of formula III may be formed by reacting cis-[PtCl$_2$(L$^1$)$_2$] with the amine ligand L$^2$ in aqueous solution, or in other suitable solvents such as described herein, and with heating.

It is a critical feature of the present invention that ligands $L^1$ and $L^2$ are in mutually trans co-ordination sites. The remaining groups or atoms in formula I may be in cis- or trans- positions, and it is believed that there may be relatively easy isomerisation between the positional isomers for the X and Y sites.

As has been mentioned, the compounds of formula I posses activity in standard in vitro and certain in vivo tests which indicate their suitability for the treatment of cancer.

The compounds of the invention may be utilised, according to the invention, as an active component in a pharmaceutical composition comprising a compound of formula I, in admixture with a pharmaceutically acceptable carrier or diluent. The invention also includes the use of a compound of formula I, for the preparation of a medicament for the treatment of cancer.

The active compounds may be administered in the form of pharmaceutical compositions formulated according to well known principles and incorporating the compound, preferably in unit dose form, in combination with a pharmaceutically acceptable diluent or carrier. Such compositions may be in the form of solutions or suspensions for injection, or be in capsule, tablet, dragee, or other solid composition or as a solution or suspension for oral administration, or formulated into pessaries or suppositories, or sustained release forms of any of the above. Suitable diluents, carriers, excipients and other components are known. It may be desirable also to formulate a composition for topical administration such as an ointment or cream, for example to be administered as a transdermal patch.

The pharmaceutical compositions according to the invention may contain dosages determined in accordance with conventional pharmacological methods, suitably to provide active compounds in the dosage range in humans of from 0.1 to 100 mg/kg body weight per day, in a single unit dose or in a number of smaller unit doses. Preferred dosage ranges are 1 to 30 mg/kg body weight per day.

The compounds may be administered alone or in combination with another chemotherapeutic agent, such as cisplatin, either as a single treatment or course of treatment or as part of combined therapy with other pharmaceuticals to overcome or diminish side effects or to improve bioavailability, or in combination with other therapies such as radiation treatment.

The invention will now be described by way of example only.

EXAMPLE 1

A suspension of cis-[PtCl$_2$(NH$_3$)$_2$] (6.0 g, 20 mmol) in water (120 ml) was treated with a slight excess of cyclopentylamine (c-C$_5$H$_9$NH$_2$; 3.5 g, 41 mmol). The mixture was stirred and heated at 80°–90° C. for 3 hours. The solution was treated with activated charcoal and filtered.

The filtrate was treated with conc HCl (ca 25 ml) and gently refluxed for around 10 hours. After cooling in an ice bath the product was collected by filtration and washed with water and dried in air then in vacuo. Yield: 6.0 g (81.5%).

The complex trans-[PtCl$_2$(NH$_3$)(c-C$_5$H$_9$NH$_2$)] product (4.0 g, 10.9 mmol) was stirred in water (80 ml) and hydrogen peroxide (30% w/v, 6 ml, 52.9 mmol) was added. A little acetone was used to aid wetting of the solid and the mixture was stirred and warmed to ca 70° C. and held at this temperature for 1.5 hours. The suspension was allowed to cool to room temperature and was then filtered.

The solid product was washed with water then with acetone and finally diethyl ether and dried in vacuo. Yield: 3.3 g (75.5%)

The product trans-[PtCl$_2$(OH)$_2$(NH$_3$)(c-C$_5$H$_9$NH$_2$)] was confirmed by HPLC, IR spectroscopy and elemental analysis.

|        | C     | H    | N    | Cl    |
|--------|-------|------|------|-------|
| calc:  | 14.93 | 3.98 | 6.97 | 17.66 |
| found: | 15.28 | 4.16 | 6.86 | 17.91 |

EXAMPLE 2

The procedure of Example 1 was followed but using cyclohexylamine in the first stage. The product trans-[PtCl$_2$(OH)$_2$(NH$_3$)(c-C$_6$H$_{11}$NH$_2$)] was confirmed by HPLC, IR spectroscopy and elemental analysis.

|        | C     | H    | N    | Cl    |
|--------|-------|------|------|-------|
| calc:  | 17.13 | 4.36 | 6.73 | 17.05 |
| found: | 17.19 | 4.11 | 6.58 | 17.45 |

EXAMPLE 3

The procedure of Example 1 was followed but using isopropylamine instead of cyclopentylamine. The product trans-[PtCl$_2$(OH)$_2$(NH$_3$)((CH$_3$)$_2$CHNH$_2$)] was confirmed by IR spectroscopy and elemental analysis.

|        | C    | H    | N    | Cl    |
|--------|------|------|------|-------|
| calc:  | 9.58 | 3.75 | 7.45 | 18.85 |
| found: | 9.43 | 3.15 | 7.08 | 19.40 |

EXAMPLE 4

The procedure of Example 1 was followed, except that tert-butylamine was used instead of cyclopentylamine. The product crystallised as the perhydrate. The product was confirmed by IR spectroscopy and elemental analysis. The basic compound was obtained by trituration with acetone and this was confirmed by IR spectroscopy and elemental analysis. The product was identified as trans-[PtCl$_2$(OH)$_2$NH$_3$(t-C$_4$H$_9$NH$_2$)].

|       | C     | H    | N    | Cl    |
|-------|-------|------|------|-------|
| calc: | 12.31 | 4.10 | 7.18 | 18.20 |
| found:| 12.10 | 4.07 | 6.94 | 18.29 |

EXAMPLE 5

The complex trans-[PtCl$_2$(OH)$_2$NH$_3$(c-C$_6$H$_{11}$NH$_2$)] (1.02 g, 2.4 mmol), the product of Example 2 was suspended in acetic anhydride (10 ml) and stirred for one week. The resulting precipitate was filtered off and washed with diethyl ether, then dried under vacuum. The product [PtCl$_2$(OCOCH$_3$)$_2$(NH$_3$)(c-C$_6$H$_{11}$NH$_2$)] believed to be the cis,cis,trans isomer was obtained in 68% yield. Its structure was confirmed by elemental analysis and by IR and Raman spectroscopy.

|       | C     | H    | N    | Cl    |
|-------|-------|------|------|-------|
| calc: | 24.00 | 4.40 | 5.60 | 14.20 |
| found | 24.16 | 4.33 | 5.52 | 14.11 |

EXAMPLE 6

The method of Example 1 was followed, but using methylamine instead of cyclopentylamine in the first step. In the second step, the reaction mixture was stirred for 5 days at room temperature. The product trans-[PtCl$_2$(OH)$_2$NH$_3$(MeNH$_2$)] was isolated and its composition and structure confirmed.

|       | C    | H    | N    | Cl    |
|-------|------|------|------|-------|
| calc: | 3.45 | 2.87 | 8.05 | 20.40 |
| found:| 3.20 | 2.12 | 7.99 | 20.54 |

EXAMPLE 7

The complex cis-[PtCl$_2$(NH$_3$)$_2$] (5 g, 16.6 mmol) was suspended in water (50 ml) and morpholine (3.2 g, 36 mmol) was added with stirring. The mixture was heated at 75° C. until all solid had dissolved and was then maintained at 50° C. for 1 hour. The mixture was then allowed to cool to room temperature.

Saturated sodium chloride solution (50 ml) and concentrated hydrochloric acid (4 equivalents to Pt, 6 ml) were added to the mixture and this was then heated to reflux for 5.5 hours. The mixture was cooled using an ice/salt bath for 1.5 hours and the product was collected by filtration. The solid was washed with ice-cold water (5×15 ml) and methanol (3×20 ml) and then dried in vacuo.

The procedure of the second step of Example 8 below was followed to yield trans-[PtCl$_2$(OH)$_2$NH$_3$-(morpholine)], which was isolated and its composition and structure confirmed.

|       | C     | H    | N    | Cl    |
|-------|-------|------|------|-------|
| calc: | 11.88 | 3.46 | 6.93 | 17.57 |
| found:| 11.67 | 3.31 | 6.89 | 17.53 |

EXAMPLE 8

A solution of cis-[PtCl$_2$(NH$_3$)$_2$] (6 g, 20 mmol) in dimethylacetamide 100 ml was treated with n-decylamine (6.36 g, 40 mmol) and heated to reflux for 1 hour. The mixture was then evaporated to dryness and the solid was re-suspended in a mixture of hydrochloric acid (50 ml, 1M) and saturated sodium chloride solution (50 ml). The mixture was heated to reflux for a total of 25 hours, during which time further concentrated hydrochloric acid (40 ml) was added. After cooling, the product t-[PtCl$_2$(NH$_3$)(C$_{10}$H$_{21}$NH$_2$)] was collected by filtration, washed with water, then dried in air and finally in vacuo. (Yield 3.88 g (43.9%)).

This product (3.5 g, 7.9 mmol) was slurried in n-heptane (10 ml) and treated with hydrogen peroxide (9 ml, 15% w/v, 40 mmol). The mixture was heated to reflux (ca 80° C.) for a total of 4 hours. After cooling overnight, the product was collected by filtration, washed with water, then dried in air and finally in vacuo. Yield 1.97 g (52.3%). The product trans-[PtCl$_2$(OH)$_2$NH$_3$(C$_{10}$H$_{21}$NH$_2$)] was identified by IR spectroscopy and its composition confirmed by elemental analysis.

|       | C     | H    | N    | Cl    |
|-------|-------|------|------|-------|
| calc: | 25.32 | 5.91 | 5.91 | 14.98 |
| found:| 24.72 | 5.51 | 5.84 | 14.89 |

EXAMPLE 9

A suspension of cis-[PtCl$_2$(NH$_3$)$_2$] (10.0 g, 33 mmol) in water (100 ml) was treated with a slight excess of n-hexylamine (n-C$_6$H$_{13}$NH$_2$; 7.8 g, 77 mmol) dissolved in ethanol (40 ml). The mixture was stirred and heated at ca 70° C. for 2 hours. The hot solution was treated with activated charcoal and filtered. The filtrate was allowed to cool and the solid formed removed by filtration. The resulting filtrate was evaporated to obtain further product. The solid was washed with a little acetone and diethyl ether and dried in air.

The solid (12.1 g) was dissolved in dimethylacetamide (100 ml) and concentrated HCl (10 ml, 120 mmol) added. The mixture was stirred and heated at gentle reflux for 1 hour. The solution was allowed to cool and filtered. The filtrate was added with stirring to water (250 ml) precipitating the product. This was collected by filtration, washed with water and dried in vacuo. t-[PtCl$_2$(NH$_3$)(n-C$_6$H$_{13}$NH$_2$)] Yield 7.38 g (58%).

The complex t-[PtCl$_2$(NH$_3$)(n-C$_6$H$_{13}$NH$_2$)] (3 g, 7.8 mmol) was dissolved in dimethylacetamide (50 ml) and hydrogen peroxide (5 equivalents, 4.5 ml, 30% w/v) added. The solution was heated to ca 90° C. and maintained at 70°–80° C. for 1 hour. The mixture was then cooled to ca 10° C. overnight and the product isolated by filtration. The solid was washed twice with water, then thoroughly with acetone and dried in vacuo. t-[PtCl$_2$(OH)$_2$NH$_3$(n-C$_6$H$_{13}$NH$_2$)] Yield 1.5 g (46%).

|       | C     | H    | N    | Cl    |
|-------|-------|------|------|-------|
| calc: | 17.22 | 4.82 | 6.70 | 16.99 |
| found:| 16.88 | 4.53 | 6.51 | 17.38 |

The above-described method was used to prepare t-[PtCl$_2$(OH)$_2$-NH$_3$(c-C$_7$H$_{13}$NH$_2$)], but using cycloheptylamine instead of n-hexylamine.

|       | C     | H    | N    | Cl    |
|-------|-------|------|------|-------|
| calc: | 19.53 | 4.69 | 6.51 | 16.51 |

|        | C     | H    | N    | Cl    |
|--------|-------|------|------|-------|
| found: | 19.59 | 4.69 | 6.47 | 16.79 |

EXAMPLE 10

A solution of cis-[PtCl$_2$(NH$_3$)$_2$] (6 g, 20 mmol) in dimethylacetamide was treated with diethylamine (2.92 g, 40 mmol) and the mixture heated to 80° C. for 30 minutes. The solution was treated with charcoal and filtered. On cooling overnight, pale yellow crystals were deposited which were collected by filtration, washed with ethyl acetate and dried in vacuo. A second crop of product was obtained by the addition of water (ca 50 ml) to the filtrate. Total yield: 4.8 g (67.4%). The structure of the product t-[PtCl$_2$(NH$_3$)(Et$_2$NH)] was confirmed by NMR spectroscopy.

The complex t-[PtCl$_2$(NH$_3$)(Et$_2$NH)] (1 g, 2.8 mmol) was dissolved in dimethylacetamide (10 ml) and treated with hydrogen peroxide (1.6 ml, 30% w/v, 14 mmol). The mixture was stirred at room temperature for 5 days during which time all the solid dissolved. The solution was extracted with diethyl ether (2×100 ml) then dichloromethane (2×100 ml) and then treated with acetone (250 ml). The solution was cooled to <10° C. overnight and yellow crystals were deposited. These were collected by filtration, washed with acetone and diethyl ether and dried in vacuo. t-[PtCl$_2$(OH)$_2$NH$_3$(Et$_2$NH)] Yield 0.54 g (49.3%).

|        | C     | H    | N    | Cl    |
|--------|-------|------|------|-------|
| calc:  | 12.31 | 4.10 | 7.18 | 18.21 |
| found: | 12.18 | 4.04 | 7.10 | 18.08 |

EXAMPLE 11

Cisplatin (6 g, 20 mmol) and silver nitrate (1 equivalent, 3.39 g) were stirred in dimethylformamide (100 ml) in the dark at room temperature for 66 hours. The precipitate of AgCl was removed by filtration and the filtrate added to quinuclidine (2.22 g, 20 mmol). The solution was purged with nitrogen for 15 minutes and the mixture stirred for 2 days, sealed from air. The solution was evaporated to dryness and the solid washed thoroughly with dichloromethane (100 ml). The solid was recrystallised twice using methanol.

This product, cis-[PtCl(NH$_3$)$_2$(quinuclidine)]NO$_3$, was dissolved in water (90 ml), filtered and the filtrate passed down a chloride-loaded anion exchange column (DOWEX 1-X8, 20–50 US mesh). After elution the solution was freeze dried to yield a white solid, cis-[PtCl(NH$_3$)$_2$(quinuclidine)]Cl. This was dissolved in hydrochloric acid (6M, 50 ml) and heated to reflux for 90 minutes. The mixture was then cooled using an icebath and the product collected by filtration. The solid was washed with water and dried in vacuo. t-[PtCl$_2$(NH$_3$)(quinuclidine)] Yield: 2.16 g (27.4%).

The product was treated according to the second step of Example 1, with concentration of the solution after heating with hydrogen peroxide in order to obtain the product. t-[PtCl$_2$(OH)$_2$NH$_3$(quinuclidine)] Yield: 0.7 g (29.8%).

|        | C     | H    | N    | Cl    |
|--------|-------|------|------|-------|
| calc:  | 19.63 | 4.20 | 6.54 | 16.59 |
| found: | 19.72 | 4.07 | 6.42 | 16.99 |

EXAMPLE 12

The complex cis-[PtCl$_2$(i-C$_3$H$_7$NH$_2$)$_2$] (1.26 g, 3.23 mmol) was dissolved in dimethylacetamide (30 ml) and cyclohexylamine (0.64 g, 6.46 mmol) added. The mixture was heated to reflux for 5 minutes to give a clear, yellow solution. Water (30 ml) and concentrated hydrochloric acid (10 ml) were added and the mixture heated to reflux for 3 hours. After cooling overnight the product was collected by filtration and washed with water and dried in vacuo. Yield: 0.31 g (22.3%).

The product complex t-[PtCl$_2$(i-C$_3$H$_7$NH$_2$)(c-C$_6$H$_{11}$NH$_2$)] (0.29 g, 0.68 mmol) was dissolved in dimethylacetamide (1 ml) and hydrogen peroxide (388 μl, 30% w/v, 3.4 mmol) added. The mixture was heated to 100° C. for 2 minutes and then allowed to cool to room temperature. The product was collected by filtration and washed with ethanol and acetone and dried in vacuo. The product was identified as t-[PtCl$_2$(OH)$_2$(i-C$_3$H$_7$NH$_2$)(c-C$_6$H$_{11}$NH$_2$)].

|        | C     | H    | N    | Cl    |
|--------|-------|------|------|-------|
| calc:  | 23.58 | 5.24 | 6.11 | 15.50 |
| found: | 22.85 | 5.21 | 6.03 | 15.66 |

EXAMPLE 13

Cisplatin (5.22 g, 17.4 mmol) was stirred in dimethylacetamide (100 ml) and warmed to 100° C. 1-Aminoadamantane (3.16 g, 21 mmol) was added and the mixture maintained at 100° C. for 1 hour. After cooling the solution was evaporated to dryness. The resulting solid was re-suspended in saturated sodium chloride solution (100 ml) and concentrated hydrochloric acid (16 ml, 174 mmol) and dimethylacetamide (20 ml) added. The mixture was heated to reflux for 12 hours. After cooling the product was collected by filtration, washed with water and ethanol and dried in vacuo. Yield: 4.53 g (60.0%).

This material was recrystallised by dissolving in boiling dimethylacetamide (ca 200 ml), cooling and treating with water. Yield: 2.6 g (34.4%).

The product complex t-[PtCl$_2$(NH$_3$)(1-aminoadamantane)] (0.94 g, 2 mmol) was stirred in dimethylacetamide (20 ml) with hydrogen peroxide (1.13 ml, 30% w/v, 5 equivalents). The mixture was heated at ca 100° C. for 4 hours. The mixture was allowed to stand to cool to room temperature. Water (ca 40 ml) was added to precipitate the product which was collected by filtration, washed with water and dried in vacuo. t-[PtCl$_2$(OH)$_2$NH$_3$-(1-aminoadadmantane).0.25DMA Yield: 0.45 g (42.8%)

|        | C     | H    | N    | Cl    |
|--------|-------|------|------|-------|
| calc:  | 26.96 | 4.90 | 6.44 | 14.50 |
| found: | 27.67 | 4.68 | 6.13 | 13.78 |

STARTING MATERIALS PREPARATION

The complex trans-[PtCl$_2$(NH$_3$)(c-C$_6$H$_{11}$NH$_2$)] (1.5 g, 3.93 mmol) was suspended in acetone (80 ml) and sodium iodide (2.35 g, 15.7 mmol added. The mixture was stirred for 2 days. The precipitate (NaCl) was removed by filtration and the filtrate evaporated to dryness. The solid was washed thoroughly with water, then a little methanol and finally diethyl ether, before drying in vacuo. Yield: 1.52 g (68%) t-[PtI$_2$(NH$_3$)(c-C$_6$H$_{11}$NH$_2$)].

The same procedure using LiBr instead of NaI was used to prepare t-[PtBr$_2$(NH$_3$)(c-C$_6$H$_{11}$NH$_2$)].

EXAMPLE 14

The complex cis-[PtCl(NH$_3$)$_2$(quinuclidine)Cl](NO$_3$) (2.52 g, 5.7 mmol) was stirred in hydrochloric acid (30 ml, 6 M). The mixture was heated at 80°–90° C. for 35 hours. After cooling in an ice bath for 2 hours the precipitated product was collected by filtration, washed with water and dried in vacuo. trans-[PtCl$_4$(NH$_3$)(quinuclidine)] Yield: 2.26 g (84%).

|        | C     | H    | N    | Cl    |
|--------|-------|------|------|-------|
| calc:  | 18.07 | 3.44 | 6.02 | 30.51 |
| found: | 17.77 | 3.08 | 6.14 | 30.65 |

EXAMPLE 15

The complex t-[PtCl$_2$(NH$_3$)(c-C$_6$H$_{11}$NH$_2$)] (1 g, 2.6 mmol) was stirred in water (30 ml) and hydrogen peroxide (1.5 ml, 30% w/v, 5 equivalents) added. The mixture was stirred at 65° C. for 2 hours. Hydrochloric acid (1 M, 10.5 ml) was added to initially yield a clear yellow solution. After stirring for 6 hours at ambient temperature, a yellow precipitate was obtained. This was collected by filtration, washed with water three times, and then dried in vacuo. t-[PtCl$_4$(NH$_3$)(c-C$_6$H$_{11}$NH$_2$)] Yield: 0.3 g (25.3%).

|        | C     | H    | N    | Cl    |
|--------|-------|------|------|-------|
| calc:  | 15.89 | 3.53 | 6.18 | 31.35 |
| found: | 15.90 | 3.34 | 6.08 | 31.10 |

EXAMPLE 16

The complex trans-[PtCl$_2$(NH$_3$)(c-C$_6$H$_{11}$NH$_2$)] (10.0 g, 26 mmol) was added to a solution of AgNO$_3$ (9 g, 52 mmol) in water (50 mol). The mixture was stirred in the dark for 3 days at 70°–80° C. After cooling, the resulting mixture was filtered to remove AgCl. The filtrate was passed down a column of ion exchange resin to remove NO$_3^-$. (DOWEX SBR anion exchange resin, OH— form). The resultant solution was treated with hydrogen peroxide (15 ml, 30% w/v, 5 equivalents) and stirred at ambient temperature for 3 days. Excess hydrogen peroxide was destroyed by stirring with Pt black, and after filtration, the solution was evaporated to dryness to yield a pale yellow solid. This was re-dissolved in the minimum volume of water (5 ml) and re-precipitated with ethanol (20 ml). The cream-yellow precipitate was collected and dried in vacuo. trans-[Pt(OH)$_4$NH$_3$(c-C$_6$H$_{11}$NH$_2$)]

|        | C     | H    | N    |
|--------|-------|------|------|
| calc:  | 19.00 | 5.31 | 7.39 |
| found: | 18.55 | 4.10 | 6.62 |

EXAMPLE 17

Potassium tetrachloroplatinate(II) (8.41 g, 20 mmol) dissolved in water (100 ml) was treated with cyclohexylamine (7.92 g, 80 mmol) and the solution boiled for 10 minutes. After cooling the solid was collected by filtration and re-suspended in dimethylacetamide (100 ml) and further cyclohexylamine (8 g, 81 mmol) added. The mixture was heated to reflux to yield a brown solution. Concentrated hydrochloric acid (25 ml) was added and heating continued for 4 hours. After cooling a dark coloured solid was collected by filtration and washed with water. The solid was extracted with acetone (3×50 ml) which was then treated with water (250 ml) to precipitate the pale yellow product. This was collected by filtration, washed with water and dried in vacuo. t-[PtCl$_2$(c-C$_6$H$_{11}$NH$_2$)$_2$] Yield: 1.13 g (12%).

The complex t-[PtCl$_2$(c-C$_6$H$_{11}$NH$_2$)$_2$] (0.75 g, 1.6 mmol) was dissolved in dimethylacetamide (20 ml) and hydrogen peroxide (10 ml 30% w/v) added. The mixture was warmed until all the solid dissolved to yield a pale brown solution. The solution effervesced vigorously and a yellow solid was slowly formed. The solution was allowed to cool and stand at room temperature for 3 days. The product was collected by filtration, washed with water and dried in vacuo. trans-[PtCl$_2$(OH)$_2$(c-C$_6$H$_{11}$NH$_2$)$_2$] Yield: 0.58 g (72%).

|        | C     | H    | N    | Cl    |
|--------|-------|------|------|-------|
| calc:  | 28.92 | 5.62 | 5.62 | 14.26 |
| found: | 28.85 | 5.75 | 5.57 | NA    |

"NA" = not available.

Additional compounds that have been prepared utilising methods analogous to those described in the above examples are:

|        | C     | H    | N    | Cl    |
|--------|-------|------|------|-------|
| t-[PtCl$_2$(OH)$_2$NH$_3$(EtNH$_2$)] | | | | |
| calc:  | 6.63  | 3.31 | 7.73 | 19.61 |
| found: | 6.28  | 2.59 | 7.72 | 19.74 |
| t-[PtCl$_2$(OH)$_2$(NH$_3$)(exo-2-aminonorbornane)] | | | | |
| calc:  | 19.63 | 4.21 | 6.54 | 16.59 |
| found: | 19.55 | 3.96 | 6.48 | 16.78 |
| t-[PtCl$_2$(OH)$_2$NH$_3$(pyridine)] | | | | |
| calc:  | 15.15 | 2.53 | 7.07 | 17.93 |
| found: | 15.94 | 2.20 | 6.42 | 16.87 |
| t-[PtCl$_2$(OH)$_2$NH$_3$(PhCH$_2$NH$_2$)] | | | | |
| calc:  | 19.81 | 3.30 | 6.60 | 16.74 |
| found  | 20.46 | 3.16 | 6.30 | 17.37 |
| t-[PtCl$_2$(OH)$_2$NH$_3$(quinuclidine)] | | | | |
| calc:  | 19.63 | 4.20 | 6.54 | 16.59 |
| found: | 19.72 | 4.07 | 6.42 | 16.99 |

Other compounds of interest are:

|        | C     | H    | N    | Br    |
|--------|-------|------|------|-------|
| t-[PtBr$_2$(OH)$_2$NH$_3$(c-C$_6$H$_{11}$NH$_2$)] | | | | |
| calc:  | 14.26 | 3.56 | 5.54 | 31.66 |
| found: | 14.43 | 3.47 | 5.53 | 31.52 |

|        | C     | H    | N    | Cl    |
|--------|-------|------|------|-------|
| t-[PtCl$_2$(O$_2$CCF$_3$)$_2$NH$_3$(c-C$_6$H$_{11}$NH$_2$)] | | | | |
| calc:  | 19.74 | 2.63 | 4.61 | 11.68 |
| found: | 19.40 | 2.48 | 4.55 | 12.45 |
| t-[PtCl$_2$(O$_2$CNHEt)$_2$NH$_3$(c-C$_6$H$_{11}$NH$_2$)] | | | | |
| calc:  | 25.87 | 5.02 | 10.03 | 12.72 |

|       |       |      |      |       |
|-------|-------|------|------|-------|
| found: | 25.67 | 5.00 | 9.69 | 13.07 |

The following complexes have also been prepared:

| ttt and c,c,t -[PtCl$_2$(OAc)$_2$NH$_3$(c-C$_5$H$_9$NH$_2$] | | | | |
|---|---|---|---|---|
|  | C | H | N | Cl |
| ttt-[PtCl$_2$(OAc)$_2$(i-C$_3$H$_7$NH$_2$)$_2$] | | | | |
| calc: | 23.90 | 4.78 | 5.58 | 14.14 |
| found: | 23.72 | 4.92 | 5.55 | 14.31 |
| ttt-[PtCl$_2$(OAc)$_2$NH$_3$(i-C$_3$H$_7$NH$_2$)] | | | | |
| calc: | 18.27 | 3.94 | 6.09 | 15.41 |
| found: | 18.16 | 3.72 | 5.87 | 15.42 |

The compounds of the invention were found to be active in in vitro screening tests according to the testing protocol described by L R Kelland et al, Proc A A C R, 30, 609(1989), demonstrating the ability to kill cancer cells. They were then tested in vivo in mice having Adj/PC6 tumours, L1210 lymphoid leukemia or a L1210 leukaemia variant which had been made resistant to cisplatin. The Adj/PC6 testing was carried out as described by P M Goddard et al presented in Sixth NCI-EORTC Symposium on New Drugs in Cancer Therapy 1989, which is a development of the basic method described by T A Connors et al, Chem Biol Interact 5, 415(1972). The in vivo L1210 tests were conducted according to the NCI protocol, Cancer Chemotherapy Reports, Part 3, vol 2, (Sept 1972) except that the animals used were DBA/2 mice and that dosing was carried out on days 1, 5 and 9. The animals were sacrificed when moribund. The compounds were administered parenterally (ip).

In the Adj/PC6 testing, LD$_{50}$ and ED$_{90}$ values in mg/kg body weight were determined in the conventional manner. The therapeutic index (TI) was calculated as the ratio of LD$_{50}$ to ED$_{90}$, and the results are shown below.

| Compound | LD$_{50}$ | ED$_{90}$ | TI |
|---|---|---|---|
| EX 2 | 8.8 | 0.76 | 11.6 |
| EX 3 | 18 | 10.5 | 1.7 |
| EX 4 | 35 | 4.7 | 7.4 |
| A | 15.5 | <6.25 | >2.5 |
| EX 7 | 82 | 94 | <1 | compound A is t-[PtCl$_2$(OH)$_2$NH$_3$(exo-2-aminonorbornane)].

The compound of Example 2 was tested against L1210 leukemia, and also against a strain of L1210 resistant to cisplatin, in mice, and the increase in life span (ILS) determined against control mice not being administered any active compound, according to the equation, $$ILS = \frac{T-C}{C} \times 100\%$$

where
T=days survival of treated mice and
C=days survival of control mice

| Compound | L1210 | | Resistant L1210 | |
|---|---|---|---|---|
|  | Dose | ILS | Dose | ILS |
| Ex 2 | 9 mg/kg | 77% | 9 mg/kg | 39% |

It is accepted in the art that any ILS greater than 25% is significant.

Additional tests were carried out in vivo using the compound of Example 2, against sensitive Adj/PC6 tumour cell lines, and against tumour cell lines resistant to various platinum anti-tumour agents, and a TI (Therapeutic Index) calculated, as described above. For comparison, the cis-isomer of the compound of Example 2 was tested in identical manner, and the results are shown below:

| Compound | Tumour | LD$_{50}$ (mg/kg) | ED$_{90}$ (mg/kg) | TI |
|---|---|---|---|---|
| EX 2 | Adj/PC6 | 8.8 | 0.76 | 11.6 |
|  | Adj/PC6/cisplatin res | 10.5 | 5.6 | 1.88 |
|  | Adj/PC6/iproplatin res | 8.8 | 2.6 | 3.4 |
|  | Adj/PC6/tetraplatin res | 8.8 | — | NA |
| Cis-isomer | Adj/PC6 | 17.5 | 1.4 | 13 |
|  | Adj/PC6/cisplatin res | 8.8 | — | NA |
|  | Adj/PC6/iproplatin res | 8.8 | — | NA |
|  | Adj/PC6/tetraplatin res | >12.5 | 12 | >1 |

Notes:
"—" indicates 90% inhibition not achieved for doses up to LD$_{50}$;
"NA" indicates not available.

It can be seen that the trans-isomer possesses activity, and a different spectrum of activity to the cis isomer, which would not have been expected by the skilled man.

Additional in vitro biological testing was conducted using cell lines derived from human carcinomas and maintained at the Institute of Cancer Research, Sutton, England (see C A Hills & colleagues, Br J Cancer 59, 527–34 (1989)). Monolayer cells were trypsinized and seeded in 96-well microtiter plates at a density of $1 \times 10^4$ cells/well in 200 µl of growth medium. Cells were incubated overnight and test compounds were added to triplicate wells at various concentrations for a total of 48 to 96 hours. For toxicity analysis after drug exposure, the cells were fixed with trichloroacetic acid and stained for cellular protein content by incubation for 30 minutes with 0.4% (wt/vol) sulforodamine B (SRB) dissolved in 1% acetic acid. The unbound dye was removed by 1% acetic acid washes, and the bound dye was extracted with 10 mM Tris buffer. The amount of dye in solution was quantified by absorbance at 564 nm.

In the Tables A and B below, all the cells are ovarian cancer cells with the exception of GCT27$^R$/GCT27 which are testicular. Table A gives IC$_{50}$ values in µM; Table B gives Resistance Factors as a ratio of IC$_{50}$ for a cell line bred to be resistant to cisplatin against IC$_{50}$ for the nonresistant cell line.

TABLE A

| | IC$_{50}$ (µM) Cell Line | | | | | | | | |
|---|---|---|---|---|---|---|---|---|---|
| Compound | HX62 | SKOV-3 | PXN/94 | 41M Ⓡ | 41M | CHI Ⓡ | CHI | A$_{2780}$ Ⓡ | A$_{2780}$ |
| EX 2 | 5.9 | 8.8 | 3.7 | 1.8 | 1.5 | 2.2 | 1.4 | — | — |
| EX 3 | 14 | 9.2 | 8.3 | 4.6 | 3.2 | 5.5 | 2.4 | — | — |

TABLE A-continued

| Compound | HX62 | SKOV-3 | PXN/94 | 41M ® | 41M | CHI ® | CHI | $A_{2780}$ ® | $A_{2780}$ |
|---|---|---|---|---|---|---|---|---|---|
| EX 4 | 1.8 | 4.7 | 3 | 0.9 | 1.1 | 1.6 | 0.74 | — | — |
| A | 5.6 | 4.4 | 3.2 | 1.47 | 1.4 | 1.7 | 1.4 | — | — |
| EX 7 | 100 | 47 | 50 | 54 | 26 | 28.3 | 17.3 | 47 | 10.9 |
| B | 10.2 | 8.2 | — | 1.35 | 1.3 | 1.95 | 1.12 | 4.2 | 1.06 |
| EX 6 | 110 | 72 | — | 33 | 5.4 | 30.5 | 12.5 | 64 | 6.2 |
| EX 1 | 10.2 | 7.0 | — | 1.3 | 1.1 | 1.9 | 1.15 | 5.2 | 0.95 |
| EX 8 | 23 | 25 | — | 5.3 | 12 | 14.6 | 14 | 14.1 | 2.9 |
| EX 10 | 3.2 | 12.1 | — | 0.8 | 1.8 | 4.6 | 3.3 | 11.6 | 1.9 |
| EX 11 | 40 | 27 | — | 9.5 | 14.4 | 14.3 | 10.2 | 16 | 3.2 |

("—" indicates data not available)
Compound A is t-[PtCl$_2$(OH)$_2$NH$_3$(exo-2-aminonorbornane)].
Compound B is t-[PtCl$_2$(OH$_2$)NH$_3$(PhCH$_2$NH$_2$)].

TABLE B

| | Resistance Factors Cell Lines | | | |
|---|---|---|---|---|
| Compound | 41M ®/41M | CHI ®/CHI | $A_{2780}$ ®/ $A_{2780}$ | GCT27 ®/ GCT27 |
| EX 2 | 1.2 | 1.6 | 7.1 | 1.8 |
| EX 3 | 1.4 | 2.3 | ND | ND |
| EX 4 | 0.8 | 2.2 | ND | ND |
| A | 1.0 | 1.2 | ND | ND |
| EX 7 | 2.1 | 1.6 | ND | ND |
| B | 1.0 | 1.7 | 4.0 | ND |
| EX 6 | 6.1 | 2.4 | 10.3 | ND |
| EX 1 | 1.2 | 1.7 | 5.5 | ND |
| Cisplatin (comparison) | 4.7 | 6.4 | 15.7 | 6.2 |

("ND" indicates "not determined").

It can be seen from Table B that the novel trans compounds of the invention retain significant activity against cell lines which are resistant to the commercial anti-cancer drug cisplatin.

The compound of Example 2 was used in further in vivo testing against a xenograft of OVCAR-3, an ovarian carcinoma known to be a refractory tumour, that is difficult to treat. For increasing doses, the tumour volume in treated mice was measured after 28 days, and compared to the tumour volume for a control group receiving no drug. The "growth delay" was also measured which represents the delay in achieving a doubling of the tumour volume for the treated group compared to the control group. Methodology is as described by K R Harrap et al, Adv Enzyme Reg, 31, 31–43 (1991). The results are given below.

| Compound | Dose (mg/kg) | T/C (day 28) | Growth Delay (days) |
|---|---|---|---|
| EX 2 | 1 | 0.80 | 0.9 |
| | 2 | 0.64 | 12.0 |
| | 4 | 0.48 | 16.8 |
| Cis Analogue* | 2 | 0.636 | 4.3 |
| | 4 | 0.427 | 15.2 |
| | 8 | 0.599 | 5.5 |

*The cis-analogue of the compound of Example 2 is ctc-[PtCl$_2$(OH)$_2$NH$_3$-(c-C$_6$H$_{11}$NH$_2$)].

It can be seen that the trans compound of Example 2, shows a clear dose-related effect.

I claim:

1. A trans-Pt(IV) compound of general formula I $$PtX_2Y_2L^1L^2 \qquad I$$

in which each of $L^1$ and $L^2$ is an amine ligand, provided that $L^1$ and $L^2$ are not both NH$_3$, and
each of X and Y is a halogen, hydroxyl, or a carboxylate, or both Y's together form a dicarboxylate or both X's and both Y's together form dicarboxylates in which the ligands $L^1$ and $L^2$ are in mutually trans co-ordination sites on the platinum atom.

2. A compound as claimed in claim 1, wherein in formula I, X is chlorine.

3. A compound as claimed in claim 1, wherein in formula I, Y is chlorine or hydroxyl.

4. A compound as claimed in claim 3, wherein in formula I, Y is hydroxyl.

5. A compound as claimed in claim 1, wherein in the formula I, the ligand $L^1$ and/or $L^2$ is a primary amine R-NH$_2$, in which R is straight chain alkyl, branched chain alkyl or cycloalkyl.

6. A compound according to claim 5, wherein ligand $L^1$ and/or $L^2$ is a primary amine R-NH$_2$, in which R is cycloalkyl.

7. The compound of claim 1 which is trans-[PtCl$_2$(OH)$_2$(NH)$_3$(c-C$_5$H$_9$NH$_2$)].

8. The compound of claim 1 which is trans-[PtCl$_2$(OH)$_2$(NH$_3$)(c-C$_6$H$_{11}$NH$_2$)].

9. The compound of claim 1 which is trans-[PtCl$_2$(OH)$_2$NH$_3$)((CH$_3$)$_2$CHNH$_2$)].

10. The compound of claim 1 which is trans-[PtCl$_2$(OH)$_2$(NH$_3$)((CH$_3$)$_3$CNH$_2$)].

11. The compound of claim 1 which is trans-[PtCl$_2$(OCOCH$_3$)$_2$(NH$_3$)(c-C$_6$H$_{11}$NH$_2$)].

12. A pharmaceutical composition comprising the trans-Pt(IV) compound of claim 1, in admixture with a pharmaceutically acceptable diluent or carrier.

13. The composition of claim 12, in unit dosage form.

14. A process for the production of a compound of formula I as defined in claim 1, comprising reacting a trans-Pt(II) compound of formula II, $$\text{trans-}\{PtX_2L^1L^2\} \qquad II$$

in which $L^1$ and $L^2$ are as defined in claim 15, and X is a halogen atom,
with a source of the desired group Y, and, where $X_2$ is (OH)$_2$ replacing the halogen atoms with hydroxyl, and, where Y and/or X is carboxylate or $X_2$ and/or $Y_2$ are dicarboxylate, acylating the corresponding compound of formula I in which $Y_2$ or $X_2$ and $Y_2$ (OH)$_2$ using a monofunctional or difunctional acylating agent.

* * * * *